United States Patent [19]
Sardana et al.

[11] Patent Number: 5,861,297
[45] Date of Patent: Jan. 19, 1999

[54] DETERGENT-FREE HEPATITIS C PROTEASE

[75] Inventors: Vinod V. Sardana, Lansdale; Jeffrey T. Blue, Hatfield, both of Pa.

[73] Assignee: Merck & Co., Inc., Rahway, N.J.

[21] Appl. No.: 936,865

[22] Filed: Sep. 24, 1997

Related U.S. Application Data

[60] Provisional application No. 60/027,274 Sep. 27, 1996.

[51] Int. Cl.⁶ .................. C12N 9/50; C12N 9/00
[52] U.S. Cl. ............................. 435/219; 435/183
[58] Field of Search ...................... 435/183, 219

[56] References Cited

U.S. PATENT DOCUMENTS 5,371,017  12/1994  Houghton et al. .................. 435/320.1

FOREIGN PATENT DOCUMENTS

WO 95/22985  2/1994  WIPO .

OTHER PUBLICATIONS

E. M. Wondrak et al., *FEBS Letters*, 280(2); pp. 347–350 (1991).
C. Lin et al., *Nat Acad. of Sci.*, 92; pp. 7622–7626 (1995).
E. D. A. D'Souza et al., *J. Gen Virology*, 76(2); pp. 1729–1736 (1995).
I. Shoji et al., *Hepatology*, 22(6), pp. 1648–1655 (1995).

*Primary Examiner*—Karen Cochrane Carlson
*Attorney, Agent, or Firm*—Sylvia A. Ayler; Mark R. Daniel

[57] ABSTRACT

The protease of Hepatitis C virus (HCV) is purified without detergent, and is useful as a screening tool for HCV antivirals as well as a diagnostic tool for diseases resulting from HCV infection.

3 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
    ( A ) LENGTH: 631 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
    ( A ) ORGANISM: Hepatitis C. Virus
    ( B ) STRAIN: NS3 Serine Protease Domain
    ( C ) INDIVIDUAL ISOLATE: BK ( v i i ) IMMEDIATE SOURCE:
    ( A ) LIBRARY: described by Tomei et al. in 1993
    ( B ) CLONE: cDNA clone pCD (38- 9.4)

( v i i i ) POSITION IN GENOME:
    ( B ) MAP POSITION: 1-180

( x i ) SEQUENCE DESCRIPTION: SEQ ID NO:1:

```
Ala Pro Ile Thr Ala Tyr Ser Gln Gln Thr Arg Gly Leu Leu Gly Cys
 1               5                  10                  15

Ile Ile Thr Ser Leu Thr Gly Arg Asp Lys Asn Gln Val Glu Gly Glu
             20                  25                  30

Val Gln Val Val Ser Thr Ala Thr Gln Ser Phe Leu Ala Thr Cys Val
         35                  40                  45

Asn Gly Val Cys Trp Thr Val Tyr His Gly Ala Gly Ser Lys Thr Leu
     50                  55                  60

Ala Gly Pro Lys Gly Pro Ile Thr Gln Met Tyr Thr Asn Val Asp Gln
65                  70                  75                  80

Asp Leu Val Gly Trp Gln Ala Pro Pro Gly Ala Arg Ser Leu Thr Pro
                 85                  90                  95

Cys Thr Cys Gly Ser Ser Asp Leu Tyr Leu Val Thr Arg His Ala Asp
             100                 105                 110

Val Ile Pro Val Arg Arg Arg Gly Asp Ser Arg Gly Ser Leu Leu Ser
         115                 120                 125

Pro Arg Pro Val Ser Tyr Leu Lys Gly Ser Ser Gly Gly Pro Leu Leu
     130                 135                 140

Cys Pro Ser Gly His Ala Val Gly Ile Phe Arg Ala Ala Val Cys Thr
145                 150                 155                 160

Arg Gly Val Ala Lys Ala Val Asp Phe Val Pro Val Glu Ser Met Glu
                 165                 170                 175

Thr Thr Met Arg Ser Pro Val Phe Thr Asp Asn Ser Ser Pro Pro Ala
             180                 185                 190

Val Pro Gln Ser Phe Gln Val Ala His Leu His Ala Pro Thr Gly Ser
         195                 200                 205

Gly Lys Ser Thr Lys Val Pro Ala Ala Tyr Ala Ala Gln Gly Tyr Lys
     210                 215                 220
```

```
Val Leu Val Leu Asn Pro Ser Val Ala Ala Thr Leu Gly Phe Gly Ala
225             230             235                         240

Tyr Met Ser Lys Ala His Gly Ile Asp Pro Asn Ile Arg Thr Gly Val
                245             250                 255

Arg Thr Ile Thr Thr Gly Ala Pro Val Thr Tyr Ser Thr Tyr Gly Lys
            260             265                 270

Phe Leu Ala Asp Gly Gly Cys Ser Gly Gly Ala Tyr Asp Ile Ile Ile
            275             280                 285

Cys Asp Glu Cys His Ser Thr Asp Ser Thr Thr Ile Leu Gly Ile Gly
    290             295                 300

Thr Val Leu Asp Gln Ala Glu Thr Ala Gly Ala Arg Leu Val Val Leu
305             310             315                         320

Ala Thr Ala Thr Pro Pro Gly Ser Val Thr Val Pro His Pro Asn Ile
                325             330                 335

Glu Glu Val Ala Leu Ser Asn Thr Gly Glu Ile Pro Phe Tyr Gly Lys
            340             345                 350

Ala Ile Pro Ile Glu Ala Ile Arg Gly Gly Arg His Leu Ile Phe Cys
            355             360                 365

His Ser Lys Lys Lys Cys Asp Glu Leu Ala Ala Lys Leu Ser Gly Leu
    370             375                 380

Gly Ile Asn Ala Val Ala Tyr Tyr Arg Gly Leu Asp Val Ser Val Ile
385             390             395                         400

Pro Thr Ile Gly Asp Val Val Val Ala Thr Asp Ala Leu Met Thr
                405             410                 415

Gly Tyr Thr Gly Asp Phe Asp Ser Val Ile Asp Cys Asn Thr Cys Val
            420             425                 430

Thr Gln Thr Val Asp Phe Ser Leu Asp Pro Thr Phe Thr Ile Glu Thr
            435             440                 445

Thr Thr Val Pro Gln Asp Ala Val Ser Arg Ser Gln Arg Arg Gly Arg
    450             455                 460

Thr Gly Arg Gly Arg Arg Gly Ile Tyr Arg Phe Val Thr Pro Gly Glu
465             470             475                         480

Arg Pro Ser Gly Met Phe Asp Ser Ser Val Leu Cys Glu Cys Tyr Asp
                485             490                 495

Ala Gly Cys Ala Trp Tyr Glu Leu Thr Pro Ala Glu Thr Ser Val Arg
            500             505                 510

Leu Arg Ala Tyr Leu Asn Thr Pro Gly Leu Pro Val Cys Gln Asp His
    515             520                 525

Leu Glu Phe Trp Glu Ser Val Phe Thr Gly Leu Thr His Ile Asp Ala
    530             535                 540

His Phe Leu Ser Gln Thr Lys Gln Ala Gly Asp Asn Phe Pro Tyr Leu
545             550             555                         560

Val Ala Tyr Gln Ala Thr Val Cys Ala Arg Ala Gln Ala Pro Pro Pro
                565             570                 575

Ser Trp Asp Gln Met Trp Lys Cys Leu Ile Arg Leu Lys Pro Thr Leu
            580             585                 590

His Gly Pro Thr Pro Leu Leu Tyr Arg Leu Gly Ala Val Gln Asn Glu
            595             600                 605

Val Thr Leu Thr His Pro Ile Thr Lys Tyr Ile Met Ala Cys Met Ser
    610             615                 620

Ala Asp Leu Glu Val Val Thr
625             630
```

( 2 ) INFORMATION FOR SEQ ID NO:2:

(i) SEQUENCE CHARACTERISTICS:
    (A) LENGTH: 54 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
    (A) LIBRARY: cDNA clone (See Seq. ID No:1)
    (B) CLONE: NS4A Protein (xi) SEQUENCE DESCRIPTION: SEQ ID NO:2:

```
Ser Thr Trp Val Leu Val Gly Gly Val Leu Ala Ala Leu Ala Ala Tyr
1               5                   10                  15
Cys Leu Thr Thr Gly Ser Val Val Ile Val Gly Arg Ile Ile Leu Ser
            20                  25                  30
Gly Arg Pro Ala Ile Val Pro Asp Arg Glu Leu Leu Tyr Gln Glu Phe
        35                  40                  45
Asp Glu Met Glu Glu Cys
    50
```

(2) INFORMATION FOR SEQ ID NO:3:

(i) SEQUENCE CHARACTERISTICS:
    (A) LENGTH: 34 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vii) IMMEDIATE SOURCE:
    (A) LIBRARY: Cofactor of NS3 serine protease
    (B) CLONE: Solid phase peptide synthesis (xi) SEQUENCE DESCRIPTION: SEQ ID NO:3:

```
Gly Ser Val Val Ile Val Gly Arg Ile Ile Leu Ser Gly Arg Pro Ala
1               5                   10                  15
Ile Val Pro Asp Arg Glu Val Leu Tyr Gln Glu Phe Asp Glu Met Glu
            20                  25                  30
Glu Asx
```

DETERGENT-FREE HEPATITIS C PROTEASE

This application is a continuation of provisional application Ser. No. 60/027,274, filed Sep. 27, 1996, now abandoned.

BACKGROUND OF THE INVENTION

Hepatitis C virus (HCV) infection is found in 0.5% to 8.0% of blood donors worldwide. Because the infection is chronic in more than 60% of infected persons, the disease is an important public health and economic problem. The management of patients with chronic hepatitis C is complex—the disease is often only mildly symptomatic and slowly progressive, but 20% of patients develop cirrhosis after 20 years of infection and perhaps 10% of those with cirrhosis develop hepatocellular carcinoma. It is also an important indication for liver transplantation. In Europe and Japan the disease is more important numerically than is either hepatitis B or HIV infection. Existing antiviral agents are effective in only a minority of patients, yet good responses can be obtained.

An important target for the treatment of HCV is nonstructural protein 3, a protease encoded by HCV. This NS3 protease associated with human hepatitis C virus is an unstable protein in the absence of high concentrations of detergent. To stabilize the NS3 protease to sufficient quantities for biochemical, kinetic, and biophysical analyses, as well as for the construction of antiviral screening assays, ionic or non-ionic detergents need be incorporated both during purification and analyses. Antiviral leads discovered with detergent treated NS3 protein are not useful. Further, the presence of high quantities of detergents renders significant difficulties in the precise interpretations of biochemical, kinetic, and biophysical analyses. In some cases (e.g., sedimentation, protein crystallization), the presence of detergents preclude biochemical, kinetic, and biophysical analyses.

Prior methods employed detergents and glycerol for purification of NS3. Applicants have discovered a method of purifying NS3 without detergent, with from 5% to about 20% glycerol, preferably 7–12% and with high stability and activity. The resultant enzyme displays a higher catalytic activity than what is known for this protease, that is, 10–500 fold more active than the prior art preparations, depending on the form of the enzyme. Purification according to the methods of the present invention ensures a high stability of the NS3 protease, rendering it amenable to kinetic, biochemical, and biophysical analyses in the absence of detergents. Prior art methods do not afford a stable, detergent free NS3 for enzymologic, biochemical, and biophysical studies.

When properly expressed and prepared from the cloned plasmid in *E. coli*, the NS3 protease is obtained in milligram quantities in the complete absence of detergent. The resultant enzyme is very soluble and stable for long periods of time (weeks to months at 4° C. and >12 months at –80° C.), and displays high catalytic activity.

An assay with the detergent free HCV NS3 protease is useful as a screening tool for HCV antivirals as well as a diagnostic tool for diseases resulting from HCV infection. The potency range of the HCV antivirals can range from subnanomolar to micromolar concentrations.

BRIEF DESCRIPTION OF THE INVENTION

Detergent free NS3 protease of Hepatitis C virus (HCV) is prepared, and a screening assay for the protein inhibitors is constructed. The detergent free NS3 protease is useful as a screening tool for HCV antivirals, as well as a diagnostic tool for diseases resulting from HCV infection.

DETAILED DESCRIPTION OF THE INVENTION

ABBREVIATIONS AND DEFINITIONS

| | |
|---|---|
| HCV | Hepatitis C Virus |
| IPTG | Isopropyl-D(−)thiogalactopyranoside |
| NS3 | Nonstructural protein 3 of Hepatitis C virus |
| PMSF | Phenylmethylsulfonyl fluoride |
| EDTA | ethylendiammino-tetraacetic acid |
| DTT | dithiothreitol |
| r.p.m. | Revolutions per minute |
| PAGE | Polyacrylamide gel |
| SDS | Sodium dodecylsulfate |
| NS | non-structural |
| HPLC | High Performance Liquid Chromatography |

In one aspect of the invention a stable, detergent free HCV NS3 protease is claimed.

In another aspect of the invention a screening assay for the detection of compounds that inhibit HCV NS3 protease is claimed.

In still another aspect of the invention, the compounds that inhibit HCV NS3 protease as measured by the screening assay of claim 2 are claimed.

In yet another aspect of the invention, a process for purifying active HCV NS3 protease without detergent is claimed.

There is disclosed stable, detergent free nonstructural protein 3 of Hepatitis C virus, also known as NS3 protease of HCV or NS3. The NS3 protease is useful screening tool for HCV antivirals, as well as a diagnostic tool for diseases resulting from HCV infection.

One utility for HCV NS3 protease is a screening assay for the detection of compounds that inhibit HCV NS3 protease. This assay has a procedure comprising the steps of:
(a) providing a quantity of a compound or compounds to be assayed;
(b) incubating said compound or compounds with detergent free HCV NS3 protease in an HCV NS3 protease assay;
(c) determining the inhibition of said protease in the HCV NS3 protease substrate cleavage assay.

Also encompassed in the present invention are compounds that substantially inhibit the HCV NS3 protease.

This invention also relates to a process for purifying active HCV NS3 protease without detergent and with from 5% to about 20% glycerol, comprising the steps of:
(a) providing a quantity of cells expressing HCV NS3 protease;
(b) disrupting the cells to form a suspension in buffer without detergent;
(c) centrifuging the suspension to remove particulate matter;
(d) subjecting the supernatant of step (c) to one or more steps of ion exchange chromatography under eluting buffer conditions without detergent;
(e) to give active HCV NS3 protease in buffer without detergent.

One embodiment of the process for purifying active HCV NS3 protease without detergent and with from 7% to about 12% glycerol, comprises the steps of:
(a) providing a quantity of cells expressing HCV NS3 protease;
(b) disrupting the cells with a microfluidizer to form a suspension in buffer without detergent, said buffer having pH of between about 6.5 and about 7.5;
(c) centrifuging the suspension to remove particulate matter, at between about 5000 and about 8000 r.p.m. for about 15 minutes;
(d) subjecting the supernatant of step (c) to one or more steps of cation exchange chromatography under eluting buffer conditions in a salt or pH gradient without detergent;

(e) to give active HCV NS3 protease in buffer without detergent.

The nonstructural protein 3 of Hepatitis C virus, also known as NS3 protease, can exist in active form as an enzyme or as a complex with the cofactor . It has been discovered by applicants that the complex is about 1000 times more active than the enzyme by itself. The enzyme is itself about 10 times more active than prior art preparations purified with detergent. In the screening assays of the present invention, all active forms are encompassed.

Expression of HCV NS3 Protease in a Recombinant Expression System

It is now a relatively straightforward technology to prepare cells expressing a foreign gene. Such cells act as hosts and include E. coli, B. subtilis, yeasts, fungi, plant cells or animal cells. Expression vectors for many of these host cells have been isolated and characterized, and are used as starting materials in the construction, through conventional recombinant DNA techniques, of vectors having a foreign DNA insert of interest. Any DNA is foreign if it does not naturally derive from the host cells used to express the DNA insert. The foreign DNA insert may be expressed on extra-chromosomal plasmids or after integration in whole or in part in the host cell chromosome(s), or may actually exist in the host cell as a combination of more than one molecular form. The choice of host cell and expression vector for the expression of a desired foreign DNA largely depends on availability of the host cell and how fastidious it is, whether the host cell will support the replication of the expression vector, and other factors readily appreciated by those of ordinary skill in the art.

The technology for recombinant procaryotic expression systems is now old and conventional. The typical host cell is E. coli. The technology is illustrated by treatises such as Wu, R (ed) *Meth. Enzymol.*, 68 (1979) and Maniatis, T. et al., *Molecular Cloning: A Laboratory Manual* Cold Spring Harbor 1982.

The foreign DNA insert of interest comprises a DNA sequence coding for HCV NS3 protease (or stable functional mutant thereof) of the present invention, including any synthetic sequence with this coding capacity or any such cloned sequence or combination thereof. For example, HCV peptides coded and expressed by an entirely recombinant DNA sequence is encompassed by this invention.

Vectors useful for constructing eukaryotic expression systems for the production of recombinant HCV comprise the DNA sequence for HCV or variant thereof, operatively linked thereto with appropriate transcriptional activation DNA sequences, such as a promoter and/or operator. Other typical features may include appropriate ribosome binding sites, termination codons, enhancers, terminators, or replicon elements. These additional features can be inserted into the vector at the appropriate site or sites by conventional splicing techniques such as restriction endonuclease digestion and ligation.

Yeast expression systems, which are one variety of recombinant eukaryotic expression systems, generally employ *Saccharomyces cerevisiae* as the species of choice for expressing recombinant proteins. *S. cerevisiae* and similar yeasts possess well known promoters useful in the construction of yeast expression systems, including but not limited to GAP491, GAL10, ADH2, and alpha mating factor.

Yeast vectors useful for constructing recombinant yeast expression systems for expressing HCMV include, but are not limited to, shuttle vectors, cosmids, chimeric plasmids, and those having sequences derived from 2-micron circle plasmids.

Insertion of the appropriate DNA sequence coding for HCV, into these vectors will, in principle, result in a useful recombinant yeast expression system for HCV where the modified vector is inserted into the appropriate host cell, by transformation or other means.

One preferred expression system is with baculovirus, under the control of the polyhedrin promoter or the p10 promoter. See, e.g., D.R. O'Reilly et al., *Baculovirus Expression Vectors: A Laboratory Manual* W.H. Freeman 1992, for a background description of this expression technology. This system employs the isolation of a recombinant baculovirus carrying the gene of interest. The baculovirus system is especially useful for the simultaneous expression of more than one protein.

Recombinant mammalian expression systems are another means of producing the recombinant HCV for the conjugates of this invention. In general, a host mammalian cell can be any cell that has been efficiently cloned in cell culture. Host mammalian cells useful for the purposes of constructing a recombinant mammalian expression system include, but are not limited to, Vero cells, NIH3T3, GH3, COS, murine C127 or mouse L cells. Mammalian expression vectors can be based on virus vectors, plasmid vectors which may have SV40, BPV or other viral replicons, or vectors without a replicon for animal cells. Detailed discussions on mammalian expression vectors can be found in the treatises of Glover, D.M. (ed.) "DNA Cloning: A Practical Approach," IRL 1985, Vols. I and II.

Recombinant HCV may possess additional and desirable structural modifications not shared with the same organically synthesized peptide, such as adenylation, carboxylation, glycosylation, hydroxylation, methylation, phosphorylation, myristoylation, extension or trimming of either the amino- or carboxy-terminal ends or both. These added features may be chosen or preferred as the case may be, by the appropriate choice of recombinant expression system. On the other hand, recombinant HCV may have its sequence extended by the principles and practice of organic synthesis.

Purification

In the detergent free purification process of the present invention, virtually any source of NS3 protease is suitable, whether recombinant or not. Preferred sources are recombinant, most preferred is an expression system using E. coli.

For expression systems, whether or not recombinant, the NS3 must first be isolated in a soluble fraction. Cells expressing HCV protease are disrupted in buffer to form a suspension in buffer. The disruption is carried out by any of a variety of well known techniques, including but not limited to treatment with a French press, a microfluidizer, sonicator, or self-digestion by inductive expression of lyzozyme. A preferred technique of disruption is with a microfluidizer.

Throughout the purification process without detergent, it is critical to maintain the pH of any buffer between about 6.5 and about 7.5.

The next step involves initial fractionation of the suspension of cellular debris. The suspension is treated to separate the soluble fraction from particulate matter, or such other step is performed that substantially separates soluble from insoluble protein. Appropriate techniques include, but are not limited to, centrifugation at between about 5,000 r.p.m. and about 8,000 r.p.m. for about 15 minutes, filtration, or salt precipitation with e.g. $(NH_4)_2SO_4$. It is understood that these initial fractionation procedures are well known and are subject to many variations. Appropriate modifications in the initial fractionation of NS3 are well within the skill of the art. The preferred method is centrifugation.

Initial fractionation of the suspension of cellular debris results in a supernatant as well as a precipitate or insoluble pellet. The supernatant is treated further.

The supernatant is then subjected to one or more steps of ion exchange chromatography, and, optionally, gel filtration, to give a substantially pure NS3 in buffer without detergent.

Preferred ion exchangers include, but are not limited to, cation exchangers on polystyrene, cation exchangers on dextran, cation exchangers on agarose, cation exchangers on cellulose, or heparin. The cation exchanger is typically a strongly or weakly acidic side chain residue. The ion exchanger is washed in a gradient of salt and/or pH to elute specifically NS3 protease. Preferred eluting conditions are a salt gradient.

Such ion exchange chromatography can be repeated or varied until substantially pure NS3 protease is obtained. Typically two rounds of cation exchange chromatography are employed.

Preferred storage conditions involve having the enzyme in 25 mM HEPES (pH 7.5), 10% glycerol, 10 mM DTT and approximately 300 mM sodium chloride at a concentration of ~15 uM or above at –80° C.

EXAMPLE 1

Expression of the HCV NS3 Protease

Plasmid DNA encoding amino acids 1027–1206 of the BK strain HCV polypeptide was cloned downstream of the T7-7 vector, in frame with the first ATG of the protein of gene 10 of the T7 phage, to obtain the plasmid pT7-7 ($NS3_{1027-1206}$), using methods that are known to the molecular biology practice. See PCT WO 95/22985, published Aug. 31, 1995, incorporated by reference. This plasmid was transfected into $E.\ coli$ BL21DE3 plysS cells (Novagen) utilizing the heat-shock technique. Cells were grown at 37° C. in LB medium containing 50 ug/ml ampicilin to an optical density of 0.4–0.6 at 600 nm whereupon the temperature was lowered to 25° C. and expression of NS3 was induced with 400 uM IPTG. Cells were allowed to grow further for two hours and then harvested by centrifugation and stored at –80° C. until lysis.

EXAMPLE 2

Purification of the HCV NS3 Protease in the Absence of Detergents

Cells from a 10-L culture were re-suspended in 100 ml of lysis buffer (25 mM sodium phosphate pH 7.5, 1 mM EDTA, 10% glycerol, 5 mM DTT) at 4° C. and treated with 0.02 mg/ml DNase (Type IIS: Bovine Pancreas Sigma) in 20 mM $MgCl_2$ for 30 min. PMSF (1 mM) was added to the suspension and cells were immediately disrupted by placing them 6 times through a microfluidizer at a pressure of 6 Bar. The lysate was centrifuged at 10,000 rpm for 30 min, and the supernatant was collected and loaded at onto a cation exchange column (Hi-Load SP Sepharose High Performance) pre-equilibrated in 50 mM sodium phosphate pH 6.5, 10% glycerol, 1 mM EDTA, 5 mM DTT, at a flow rate of 2.5 ml/min. The NS3 protease was eluted from the column in a 0–1 M NaCl salt gradient. Fractions were analyzed by SDS-PAGE. Fractions containing the NS3 protease were pooled and first diluted 8–10 fold into a buffer containing 25 mM sodium phosphate( pH 7.5), 10% glycerol, 5 mM DTT buffer and then loaded onto two 4×5 ml Heparin columns connected in tandem at a flow rate of 3 ml/min. The enzyme was eluted with a NaCl gradient. Fractions were analyzed by SDS-PAGE and peptide cleavage assay. Enzyme fractions containing >95% pure NS3 protease were pooled and stored at 4° C. in the elution buffer. The yield was 1–2 mg of purified enzyme per liter of $E.\ Coli$ cell culture. N-terminal sequence analyses were carried out using the Edman degradation method using an Applied Biosystem model 470A gas phase sequencer. The protease concentration was determined by. quantitative amino acid analysis.

EXAMPLE 3

HCV NS3 Substrate Cleavage Assay

The peptides (7-methoxycoumarin-4-acetyl-DEMEECASHLPYK-($\epsilon$-NHCOCH$_3$) and acetyl-DEMEECASHLPYK-($\epsilon$-NHCOCH$_3$) mimicking the NS4A/4B cleavage site was purchased from Enzyme Systems Products (Dublin, Calif.) and was >95% pure. A lysine was added to the C-terminus of the acetyl-DEMEECASHLPYK-($\epsilon$-NHCOCH$_3$) peptide to enable it soluble at high concentrations and a coumarin fluorophore was introduced to the N-terminus of the (7-methoxycoumarin-4-acetyl-DEMEECASHLPYK-($\epsilon$-NHCOCH$_3$) peptide to enhance detection of the product. The NS4B/5A substrate 7-methoxycoumarin-4-acetyl-EDASTPCSGS-Nph-L (where Nph=para-nitro phenylalanine) was purchased from Bachem Biosciences. The 4A peptide with the sequence of GSVVIVGRIILS-GRKK was also synthesized by Enzyme System Products. Peptide cleavage assays were conducted at 25° C. in 100 ul of 50 mM Hepes (pH 7.5) reaction buffer, 10 mM DTT in the presence of varying amounts of glycerol, preferrably 0% to 50% glycerol. The reaction was quenched with 100 ul of 5% phosphoric acid and the mixture was analyzed by reverse phase HPLC on a 4.6/50 mm Vydac C18 column. The cleavage products were separated using a 0.1 % phosphoric acid/acetonitrile gradient and identified by comparison of retention time with authentic peptides representing the reaction products. Cleavage of the NS4A/4B occurred at the expected Cys-Ala scissile bond. UV Absorbance of the products was monitored at 220 nM and fluorescence detection done with with excitation and emission wavelengths set at 328 nm and 393 nm, respectively. The enzyme concentrations used in the assays varied from, but not limiting to, 2 to 1000 nM depending on the reaction conditions desired. For example, the enzyme concentration in the presence of the 4A peptide varied from 2 to 50 nM and 300 to 1000 nM in the absence of the 4A peptide. In the assays with the 4A peptide as the cofactor, the enzyme was preincubated at a temperature of about 0° C. to 10° C. with the 4A peptide for 5 to 10 minutes, followed by 3 to 10 minutes at room temperature at a 10–50 fold greater concentration, before the onset of reaction. For preincubation of enzyme with the 4A peptide, the enzyme was added to the solution already containing the 4A peptide. The concentration of 4A peptide and substrate used ranged from, but not limiting to, 75 nM to 50 $\mu$M and 0.1 $\mu$M to 250 $\mu$M, respectively. All substrates were dissolved in 50 mM HEPES (pH 7.5), 30 mM DTT and 10% glycerol. The reaction was typically allowed to continue for a period of 2.5 to 15 min depending on the initial reaction rate and the sensitive detection of products.

Steady state kinetic parameters ($k_{cat}$ and $K_M$) were determined by fitting initial rates (obtained at <5% of total substrate hydrolyzed) verses substrate concentrations to the Michaelis-Menten equation. Initial velocity and steady-state conditions were strictly maintained for all reaction assays performed.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and its equivalents.

What is claimed is:

1. Stable, detergent free, and substantially pure Hepatitis C virus NS3 protease.

2. A process for purifying active HCV NS3 protease without detergent, comprising the steps of:

(a) providing a quantity of cells expressing HCV NS3 protease;

(b) disrupting the cells to form a suspension in buffer without detergent;

(c) centrifuging the suspension to remove particulate matter;

(d) subjecting the supernatant of step (c) to one or more steps of ion exchange chromatography under eluting buffer conditions without detergent;

(e) to give active HCV NS3 protease in buffer without detergent.

3. A process for purifying active HCV NS3 protease without detergent, comprising the steps of:

(a) providing a quantity of cells expressing HCV NS3 protease;

(b) disrupting the cells with a microfluidizer to form a suspension in buffer without detergent, said buffer having pH of between about 6.5 and about 7.5;

(c) centrifuging the suspension to remove particulate matter, at between about 5000 and about 8000 r.p.m. for about 15 minutes;

(d) subjecting the supernatant of step (c) to one or more steps of cation exchange chromatography under eluting buffer conditions in a salt or pH gradient without detergent;

(e) to give active HCV NS3 protease in buffer without detergent.

* * * * *